United States Patent [19]
Lidert et al.

[11] Patent Number: 5,420,318
[45] Date of Patent: May 30, 1995

[54] PREPARATION OF HIGH PURITY NEEM SEED EXTRACTS

[75] Inventors: Zev Lidert, Doylestown; Craig G. Overberger, deceased, late of Yardley, by Rosemary D. Overberger, executrix; James S. Clovis, Morrisville, all of Pa.

[73] Assignee: Rohm and Haas Company, Philadelphia, Pa.

[21] Appl. No.: 920,238

[22] Filed: Jul. 27, 1992

[51] Int. Cl.$^6$ ................................. C11B 3/10
[52] U.S. Cl. ..................... 554/193; 424/195.1; 554/14; 554/17; 554/175; 554/182; 554/191; 504/157; 504/291; 504/293; 504/297
[58] Field of Search ............ 424/195.1; 554/193, 554/17, 14, 175; 514/453, 65; 71/88; 504/157, 291, 293, 297

[56] References Cited

U.S. PATENT DOCUMENTS

| | | | |
|---|---|---|---|
| 4,325,883 | 4/1982 | Jones et al. | 554/182 |
| 4,515,785 | 5/1985 | Shimizu et al. | 424/195.1 |
| 4,556,562 | 12/1985 | Larson | 424/195.1 |
| 4,946,681 | 8/1990 | Walter | 424/195.1 |

*Primary Examiner*—José G. Dees
*Assistant Examiner*—Deborah D. Carr
*Attorney, Agent, or Firm*—Clark R. Carpenter

[57] ABSTRACT

A new process has been developed for preparing high purity neem seed extract by adsorbing aqueous solutions of neem seed extract containing azadirachtin onto a macroporous polymeric adsorbent followed by desorption using a solvent. The resulting extract, optionally formulated, is a useful insecticide for the control of foliar pests.

17 Claims, No Drawings

PREPARATION OF HIGH PURITY NEEM SEED EXTRACTS

FIELD OF THE INVENTION

This invention relates to a new process for extracting and purifying insecticidal materials from the seeds of the neem tree (*Azadirachta indica* Juss.), compositions containing such extracts and methods of their use as insecticides.

BACKGROUND OF THE INVENTION

The search for compositions which have a combination of excellent insecticidal activity and desirable low toxicity to plants and mammals is a continuing one because of factors such as the desire for compounds exhibiting greater insecticidal activity, better selectivity, low environmental impact, low production cost and effectiveness against insects resistant to many known insecticides.

Various parts of the neem (or nim) tree have long been used in India for their reputed medicinal or insecticidal properties. This subtropical tree is native to the arid regions of India, Pakistan, Sri Lanka and parts of Southeast Asia and Africa.

Although all parts of the neem tree appear to have natural resistance to pests and diseases, the seeds appear to have the greatest resistance. Formulations and extracts of the seeds have been shown to be effective against many species of crop pests including gypsy moths, Japanese beetles, aphids, tobacco budworms and boll weevils. For example, see *Chem. and Engineering News*, May 27, 1985, pp. 46-51 and *U.S. Dep. Agric., Agric. Rev. Man.*, ARM-NE-4. Neem seed extract is considered to be a broad-spectrum insecticide.

Azadirachtin and other insecticidally active neem seed components can be extracted from ground neem seeds using polar solvents such as water, methanol or ethanol. On a dry weight basis, such extracts contain typically less than 5% of azadirachtin. Due to decomposition of the active ingredients, the potency of such extracts as insecticides rapidly decreases. Thus, the utility of such neem seed extracts as useful plant protection materials is severely limited.

As disclosed in U.S. Pat. No. 4,556,562, longer shelf stability is possible to achieve by formulating crude extracts as dilute alcoholic solutions, typically containing about 0.3% of azadirachtin, and adjusting the pH of those extracts to about 3.5-6. Alternatively, as disclosed in U.S. Pat. No. 4,946,681, a method is described for stabilizing an alcoholic neem seed extract by removing water with molecular sieves.

There are several known procedures for obtaining extracts of high purity, typically containing 10-100% of azadirachtin. The common feature of all these procedures is the use of polar organic solvents, such as methanol, to obtain crude extracts from which azadirachtin is separated in a succession of process steps involving liquid-liquid extractions, phase separations, solvent strips and sometimes chromatography on silica gels. Typically, the most hydrophobic impurities such as triglycerides are removed by extracting dry crude extracts or crude extracts dissolved in 50-100% aqueous methanol with a non-polar solvent such as hexane (*Journal of Liquid Chromatography*, 10 (6), 1151 (1987)). Following this procedure, the extract is partitioned between water and a polar organic solvent which is immiscible with water, such as ethyl acetate, and the organic solvent phase stripped to yield a semi-pure extract, typically containing less than 15 to 25% of azadirachtin, having a limited storage stability. Chromatography on silica gel, florasil and the like is typically required in order to obtain higher purity compositions of azadirachtin.

This known methodology is impractical and costly when it is scaled-up because it requires the handling of large volumes of flammable solvents relative to the quantity of azadirachtin that is recovered. The problems are aggravated by the fact that polar organic solvents such as methanol extract a great many accompanying impurities which subsequently need to be separated in order to prevent rapid decomposition of azadirachtin in such extracts.

Replacement of the alcohol extraction solvent with water would significantly reduce the extractability of many hydrophobic impurities and, in addition, would eliminate the flammability issue. However, despite the knowledge of the ability of water to extract azadirachtin from ground neem seeds, there are no published methods which take advantage of this fact. The reason for this is that separation of a clear aqueous extract from the extracted neem cake is very slow if it is done by commonly used filtration methods. Additionally, all attempts to extract azadirachtin from the aqueous filtrate with a polar organic solvent such as ethyl acetate fail due to the formation of stable emulsions which are difficult to break down.

Therefore, there remained a need for a practical, scalable and economical method that yields a solvent free composition in which azadirachtin is present in over a 15% concentration. Such a composition should possess a sufficient stability that would allow it to be used in a wide variety of insecticidal applications or, if necessary, would be amenable to further stabilization by simple chemical methods.

SUMMARY OF THE INVENTION

It has now been discovered that adsorption of an aqueous or alcoholic neem extract onto a macroporous polymeric adsorbent followed by desorption with a solvent constitutes a practical, scalable and economic process for obtaining a solvent free composition possessing over a 15% concentration of azadirachtin.

DETAILED DESCRIPTION OF THE INVENTION

Clear aqueous extracts from neem seeds containing azadirachtin can be obtained by stirring ground neem seeds or deoiled neem cake with water and then separating the liquid phase by centrifugal separation. From such clarified aqueous extracts, an azadirachtin-rich fraction can be obtained by contacting a clarified aqueous neem seed extract with a macroporous polymeric adsorbent. As used herein, macroporous polymeric adsorbents include macroporous or macroreticular copolymers prepared by known methods in the presence of a precipitant, such as those disclosed in Meitzner et al., U.S. Pat. No. 4,256,840 and copolymers into which large pores have been introduced by other methods, such as the technique described in U.S. Pat. No. 3,122,514. Examples of macroporous polymeric adsorbents include a polymer from divinylbenzene, a divinylbenzene/styrene copolymer, an acrylic (ester) polymer, a phenol/formaldehyde copolymer and the like. The extract containing azadirachtin is then desorbed from the resin with a solvent such as an alcohol, for example methanol, an ester, for example ethyl acetate, a ketone, for example methyl isobutyl ketone, other polar organic solvents, for example N,N-dimethylformamide (DMF) and dimethylsulfoxide (DMSO), an aromatic hydrocarbon, for example toluene, water and mixtures thereof. This procedure results in extracts containing over 15% of azadirachtin.

Preferred desorption solvents are alcohols, esters or ketones and mixtures thereof. A more preferred solvent is ethyl acetate.

If a column procedure is employed, the column may be regenerated by passing from about 20 to about 25 column volumes of water at about 6 column volumes per hour through the column to remove the desorption solvent. For example, when ethyl acetate was used as the desorption solvent, this regeneration procedure brought the ethyl acetate level in the water washings to less than 100 ppm which is sufficiently low to start a new cycle.

More particularly, neem cake obtained by mechanical extrusion of oil from crushed neem seeds can be ground and stirred with water in a ratio of about 1/6 cake/water on a weight/weight (w/w) basis. The light liquid phase can then be separated from the heavy solid phase (wetcake) by centrifugation. The wetcake can be re-slurried with more water at a ratio of about ⅓ wetcake/water (w/w) and the light liquid phase separated as before. The combined clear water extracts, typically containing less than 0.6 gram (g) of azadirachtin per liter (L), can be passed through a column packed with a macroporous polymeric adsorbent, for example a resin composed of polymeric divinylbenzene such as Amberlite ®XAD-16 resin, Amberlite XAD-4 resin, Amberchrom ®CG-161 resin and Amberchrom CG-162 resin, a divinylbenzene/styrene copolymer such as Amberlite XAD-2 resin and Duolite ®S-861 resin, an acrylic (ester) polymer such as Amberlite XAD-7 resin and Amberchrom CG-71 resin, a phenol/formaldehyde copolymer such as Duolite XAD-761 resin, and the like, at a rate of about 10 column volumes per hour for as long as is necessary to saturate the resin with azadirachtin. For example, one liter of Amberlite XAD-16 resin is capable of adsorbing approximately 20 to 40 g of azadirachtin. Following the resin saturation, about three column volumes of a solvent such as ethyl acetate are passed through the resin at a rate of about three column volumes per hour. The solvent phase can be dried, if necessary, and the solvent removed under reduced pressure to yield an azadirachtin-rich extract in which the azadirachtin is present in over 15% concentration.

If desired, the stability of the resulting azadirachtin-rich extract can be enhanced by further treatment with a mild oxidizing agent such as an alkaline solution of hydrogen peroxide, an alkyl peroxide, for example di-n-butyl peroxide, an acid peroxide, for example perbenzoic acid, sodium percarbonate or the like. Preferred solvents for this reaction are polar organic solvents such as ethyl acetate or butyl acetate. A preferred oxidizing agent is hydrogen peroxide. A preferred base used with the hydrogen peroxide is saturated sodium bicarbonate solution.

In another embodiment of this invention, a crude methanolic extract from neem seeds as is known in the art is diluted with water to a final ratio of between about 55/45 water/methanol on a volume/volume (v/v) basis to about 95/5 water/methanol (v/v), preferably to about 65/35 water/methanol (v/v) basis. The clear liquid phase is then passed through a column packed with a polymeric resin, for example a resin composed of polymeric divinylbenzene such as Amberlite XAD-16 resin, and the extract desorbed from the column as described above. If desired, the stability of the resulting azadirachtin-rich extract can be enhanced by further treatment with a mild oxidizing agent as described above.

The resulting extracts contain from about 1% to about 80% of azadirachtin, generally from about 15% to about 45% of azadirachtin.

The resulting extracts of this invention are also advantageously used in the preparation of formulations and compositions. Examples of the preparation of compositions and formulations can be found in the American Chemical Society publication "Pesticidal Formulation Research," (1969), Advances in Chemistry Series, 86 and "Pesticide Formulations," (1973), Wade Van Valkenburg editor. In these compositions and formulations, the active substance is mixed with conventional inert agronomically acceptable (i.e., plant compatible and/or pesticidally inert) diluents or extenders such as solid types usable in conventional compositions or formulations as is well known in the art. If desired, adjuvants such as surfactants, stabilizers, antifoam agents and antidrift agents may also be added.

Examples of compositions and formulations according to this invention are those known to one skilled in the art and include aqueous solutions and dispersions, oily solutions and oil dispersions, pastes, dusting powders, wettable powders, emulsifiable concentrates, flowables, granules, baits, invert emulsions, aerosol compositions and fumigating candles.

The compositions and formulations are prepared in a known manner to one skilled in the art. For example, the active compounds are extended with conventional dispersible liquid diluent carriers and/or dispersible solid carriers. If desired, carrier vehicle assistants can be used such as conventional surface-active agents including emulsifying agents and/or dispersing agents whereby, for example, organic solvents may be added as auxiliary solvents in the case where water is used as a diluent.

Adhesives such as carboxymethyl cellulose and natural and synthetic polymers, for example gum arabic, polyvinyl alcohol, polyvinyl cellulose and polyvinyl acetate, in the form of powders, granules or latices can be used in the formulations to improve the adherence of the pesticide. Furthermore, a lubricant such as calcium stearate or magnesium stearate may be added to a wettable powder or to a mixture to be granulated.

The extract of the present invention may be employed alone and/or with such solid and/or liquid dispersible carrier vehicles and/or with other known compatible active agents, especially plant protection agents such as other insecticides, arthropodicides, nematicides, fungicides, bactericides, rodenticides, herbicides, fertilizers, growth-regulating agents, synergists and the like, if desired, or in the form of particular dosage preparations for specific applications made therefrom, such as solutions, emulsions, suspensions, powders, pastes and granules which are thus ready for use.

As concerns commercially marketed preparations, these generally contemplate carrier composition mixtures in which the stabilized extract is present in an amount substantially between 0.1% and 99% by weight and preferably between about 1% and 75% by weight of the mixture.

Some formulations are capable of confering a stabilizing effect on azadirachtin in the formulated form, possibly due to dispersion, protection from humidity, sunlight and the like.

The extract formulations can be applied as sprays by methods commonly employed such as conventional high-gallonage hydraulic sprays, low gallonage sprays, ultra low volume sprays, airblast sprays, aerial sprays and dusts.

Furthermore, the present invention contemplated methods of selectively killing, combatting or controlling pests which comprise contacting insects with a correspondingly combative or toxic amount (i.e., an insect controlling or an insecticidally effective amount) of the stabilized extract of the invention alone or together with a carrier vehicle (composition or formulation) as noted above. The term "contacting" as used here is to be construed as applying to at least one of (a) such insects and (b) the corresponding habitat thereof (i.e., the locus to be protected, for example a growing crop or an area where a crop is to be grown) the active compound of this invention alone, as a constituent of a composition or formulation or as a constituent of a composition or formulation containing other insecticides or fungicides.

It will be realized, of course, that the concentration of the particular extract utilized in admixture with the carrier vehicle will depend upon such factors as the type of equipment employed, method of application, area to be treated, types of pests to be controlled and degree of infestation. In addition to the aforementioned ingredients, the preparations according to the invention may also contain other substances commonly used in preparations of this kind.

The following examples are presented to illustrate the invention and are not to be construed as limiting in scope. All parts and percentages are by weight unless otherwise indicated.

EXAMPLE 1: Extract 1(40% Azadirachtin)

Neem seeds, 1282 kilograms (kg), were partially dehulled and deoiled by standard methodology involving mechanical oil extrusion. The 586 kg of deoiled neem cake was ground in 3150 kg of water and the wetcake separated by centrifugal sedimentation. The wetcake was reslurried with 2100 kg of water and the separation repeated. The combined liquid phase, 3618 kg, was further clarified by filtration and then passed at 600 kg/hour through a stainless steel column containing 60 liters (L) of Amberlite XAD-16. The resin in the column was subsequently washed with 180 L of ethyl acetate and the resulting ethyl acetate phase was concentrated under reduced pressure to 25 kg. The ethyl acetate concentrate was then stirred with 10 kg of aqueous saturated sodium bicarbonate solution and 300 milliliters (mL) of 30% hydrogen peroxide at 55° C. for 20 minutes. The upper organic phase was separated, dried over sodium sulfate, filtered and the ethyl acetate stripped to yield 4.25 kg of Extract 1 containing 40% of azadirachtin.

EXAMPLE 2: Extract 2(27% Azadirachtin)

A crude methanolic extract, 144 kg, containing azadirachtin was prepared by extracting 200 kg of deoiled neem cake three succesive times with fresh 200 L portions of methanol. The methanol extracts were combined and partially stripped. To this resulting concentrate, 280 kg of water was added, the resulting precipitate was removed and the aqueous methanolic extract was passed through a column containing 30 L of Amberlite XAD-16 resin at a rate of 2 L per minute. The resin then was washed with 90 L of methanol. The methanol was then stripped, the resulting residue taken up in ethyl acetate and treated with an aqueous saturated solution of sodium bicarbonate containing hydrogen peroxide in the manner as described in Example 1 to yield 1.66 kg of Extract 2 containing 27% of azadirachtin.

EXAMPLE 3: Biological Activity

The extract 1 from Example 1 containing 40% of azadirachtin was tested for biological activity.

For the test, lima bean (*Phaseolus limensis* var. Woods' Prolific) plants, 2–3 weeks old, were sprayed to run-off with the test solution. After drying, the treated leaves were detached and infested with second instar larvae of Mexican Bean Beetles (MBB; *Epilachna varivestis*) and Southern Armyworms (SAW; *Spodoptera eridania*) at doses of 20, 10, 5 and 2.5 parts per million (ppm) using 5 insects/dose. The percent mortality was determined at 3 days and at 6 days.

The results obtained are as shown:

| Dosage, PPM | PERCENT MORTALITY | | | |
| --- | --- | --- | --- | --- |
| | MBB (3 Day) | MBB (6 Day) | SAW (3 Day) | SAW (6 Day) |
| 20 | 23 | 67 | 100 | 100 |
| 10 | 6 | 73 | 93 | 73 |
| 5 | 15 | 46 | 93 | 93 |
| 2.5 | 6 | 46 | 53 | 60 |

It should be understood that the instant specification and examples are set forth by way of illustration and not limitation and that various modifications and changes may be made without departing from the spirit and scope of the present invention as defined by the appended claims.

We claim:

1. A process for preparing an extract containing over 15% azadirachtin, an insecticidally active neem seed component, which comprises:
   a) stirring ground neem seeds or deoiled neem cake with water,
   b) separating the liquid phase to obtain a clarified aqueous extract,
   c) contacting said clarified aqueous neem seed extract with a macroporous polymeric adsorbent to obtain an azadirachtin-rich fraction and
   d) desorbing the extract containing azadirachtin from the macroporous polymeric adsorbent with a solvent.

2. The process of claim 1 wherein the macroporous polymeric adsorbent is a polymer of divinylbenzene, a copolymer of divinylbenzene/styrene, an acrylic polymer or a phenol/formaldehyde copolymer.

3. The process of claim 2 wherein the macroporous polymeric adsorbent is a polymer of divinylbenzene.

4. The process of claim 1 wherein the solvent is an alcohol, an ester or a ketone.

5. The process of claim 4 wherein the solvent is ethyl acetate, methanol or methyl isobutyl ketone.

6. The process of claim 5 wherein the solvent is ethyl acetate.

7. The process of claim 1 which further comprises:

e) treating the extract from step d) with an oxidizing agent.

8. The process of claim 7 wherein the oxidizing agent is an alkaline solution of hydrogen peroxide.

9. The process of claim 8 wherein sodium bicarbonate solution is used.

10. The process of claim 7 which employs a solvent in step c.

11. The process of claim 10 wherein the solvent is ethyl acetate.

12. A neem seed extract produced in accordance with the process of claim 1.

13. The extract of claim 12 wherein the extract contains from about 1% to about 80% of azadirachtin.

14. The extract of claim 13 wherein the extract contains from about 15% to about 45% of azadirachtin.

15. An insecticidal composition which comprises an agronomically acceptable carrier and an insecticidally effective amount of the extract of claim 1.

16. A process for preparing an extract containing over 15% azadirachtin, an insecticidally active neem seed component, which comprises:
   a) diluting a crude methanolic extract from neem seeds with water to obtain from about a 55/45 to about a 95/5 water/methanol extract on a volume basis,
   b) contacting said water/methanol extract with a macroporous polymeric adsorbent and
   c) desorbing the extract containing azadirachtin from the macroporous polymeric adsorbent with a solvent to obtain an azadirachtin-rich extract.

17. The process of claim 16 wherein the methanol level is about 35% on a volume basis.

* * * * *